US00PP21101P2

(12) United States Plant Patent
Ichie

(10) Patent No.: US PP21,101 P2
(45) Date of Patent: Jun. 29, 2010

(54) ***HYDRANGEA* PLANT NAMED 'LAPIS LAZULI'**

(50) Latin Name: *Hydrangea macrophylla*
Varietal Denomination: Lapis Lazuli

(76) Inventor: Toyokazu Ichie, 3-46 Hongou, Kakegawa-city, Shizuoka (JP) 436-0111

( * ) Notice: Subject to any disclaimer, the term of this patent is extended or adjusted under 35 U.S.C. 154(b) by 0 days.

(21) Appl. No.: 12/386,111

(22) Filed: Apr. 14, 2009

(51) Int. Cl.
*A01H 5/00* (2006.01)

(52) U.S. Cl. ..... Plt./250

(58) Field of Classification Search ..... Plt./250
See application file for complete search history.

*Primary Examiner*—Annette H Para
(74) *Attorney, Agent, or Firm*—Penny J. Aguirre

(57) ABSTRACT

A new cultivar of *Hydrangea macrophylla* named 'Lapis Lazuli' that is characterized by its strong blooming habit, its ability to re-bloom on new growth after deadheading, its consistently formed, hortensia type inflorescences with sterile flower sepals that are rounded to broadly ovate in shape and dark blue in color with a white central area when grown under acidic soil conditions and bright pink in color with a white central area when grown under alkaline soil conditions, its compact growth habit with strong stems that enable pot culture without the need for staking, its dark green glossy foliage and its hardiness at least in U.S.D.A. Zones 5 to 9.

2 Drawing Sheets

Botanical classification: *Hydrangea macrophylla.*
Varietal denomination: 'Lapis Lazuli'.

BACKGROUND OF THE INVENTION

The present invention relates to a new and distinct cultivar of *Hydrangea macrophylla* and will be referred to hereafter by its cultivar name, 'Lapis Lazuli'. 'Lapis Lazuli' represents a new hortensia type bigleaf *hydrangea*, a deciduous shrub grown for ornamental use in the shaded landscape and for use as a potted plant. 'Lapis Lazuli' was derived from an ongoing controlled breeding program in a nursery that focuses on new cultivars of *Hydrangea* for container and landscape use. 'Lapis Lazuli' originated as a seedling from seed sown of *Hydrangea macrophylla* by the Inventor in 1994 in Shizuoka, Japan. The parents of 'Lapis Lazuli' are unknown. The new *Hydrangea* was selected as a unique single plant from amongst the seedling evaluated in June of 2001.

Asexual reproduction of the new cultivar was first accomplished by softwood stem cuttings by the Inventor in Shizuoka, Japan in March 2006. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'Lapis Lazuli' as a unique cultivar of *Hydrangea macrophylla.*

1. 'Lapis Lazuli' is a strong bloomer and exhibits a re-blooming habit with inflorescences produced from early summer until fall with removal of spent blooms; observed in Shizuoka, Japan, Niagara on the Lake, Ontario, Canada, and Warsaw, N.C.
2. 'Lapis Lazuli' exhibits consistently formed hortensia type inflorescences that are globose in shape.
3. 'Lapis Lazuli' exhibits rounded shaped sterile flowers with sepals that are rounded to broadly ovate in shape and dark blue in color with a white central area when grown under acidic soil conditions and bright pink in color with a white central area when grown under alkaline soil conditions.
4. 'Lapis Lazuli' exhibits a compact growth habit with strong stems that enable pot culture without the need for staking.
5. 'Lapis Lazuli' exhibits dark green glossy foliage.
6. 'Lapis Lazuli' is hardy at least to U.S.D.A. Zones 5 to 9.

'Lapis Lazuli' can be most closely compared to other cultivars of *Hydrangea* that exhibit sterile flowers with sepals having white centers. The cultivar 'Pia' (not patented) is also similar in having a compact growth habit, however 'Pia' differs from 'Lapis Lazuli' in having dark pink sepals and a smaller central white area. The cultivar 'Europa' (not patented) differs from 'Lapis Lazuli' and in having very dark pink sepals that turn purple-pink in fall and in having a smaller white central area. The cultivar 'Floralia' (not patented) differs from 'Lapis Lazuli' in having a less rounded inflorescence and sepals that are convex, rosy pink in color, and in having a central area that is yellow to creamy white in color.

BRIEF DESCRIPTION OF THE DRAWINGS

The accompanying colored photographs illustrate the overall appearance and distinct characteristics of the new Hydrangea. The photographs were taken of three year-old plants of 'Lapis Lazuli' as grown outdoors in three-gallon containers in Shizuoka, Japan.

The photograph in FIG. 1 illustrates the foliage, flowering habit and inflorescences as observed when grown under acidic soil conditions.

Figure 1:
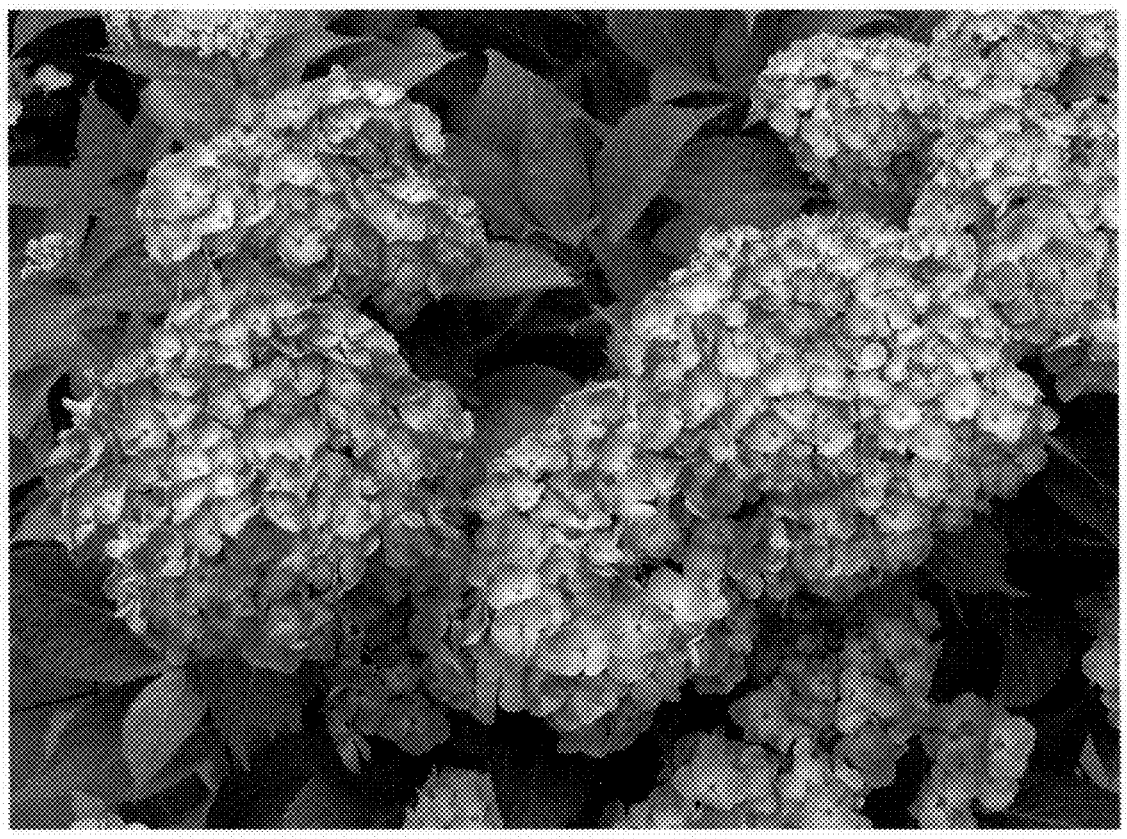
Figure 2:
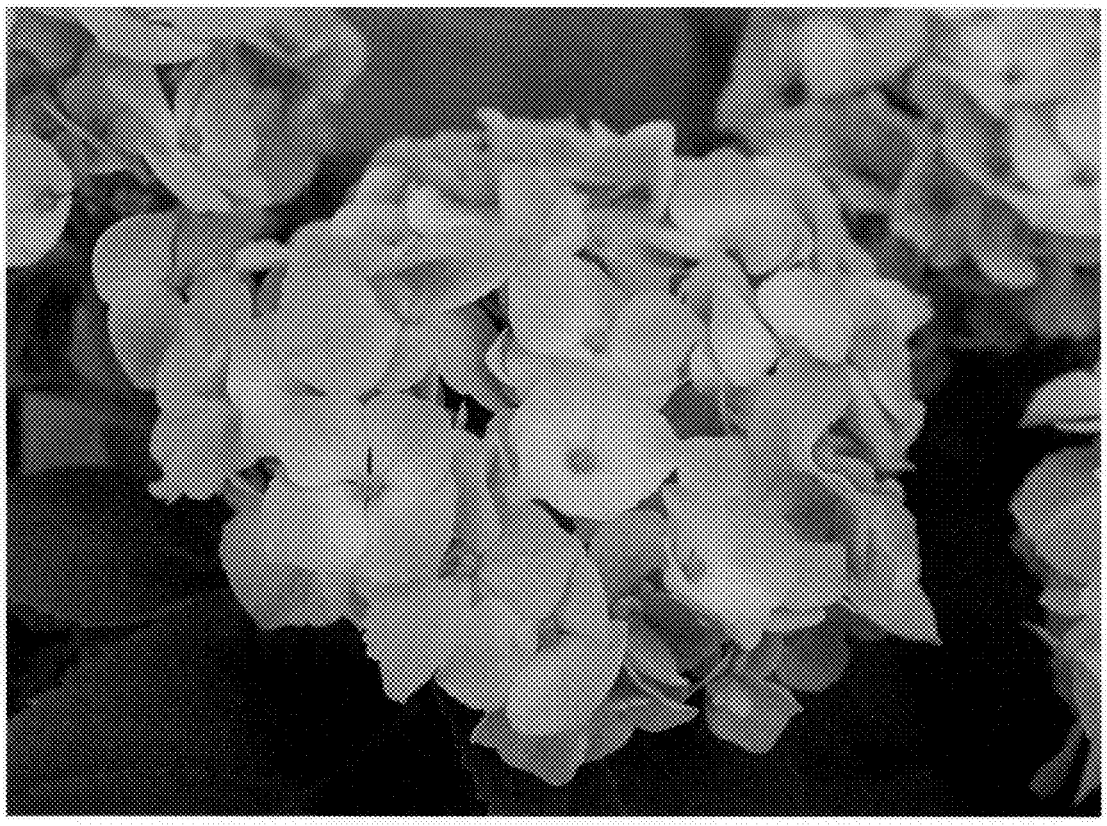

The photograph in FIG. 2 illustrates a close-up view of an inflorescence of 'Lapis Lazuli' as grown under alkaline soil conditions.

The colors in the photographs may differ slightly from the color values cited in the detailed botanical description, which accurately describe the colors of the new *Hydrangea.*

BOTANICAL DESCRIPTION OF THE PLANT

The following is a detailed description of a three year-old plants of 'Lapis Lazuli' as grown outdoors in three-gallon container in Shizuoka, Japan. The detailed data was taken from plants growing under alkaline conditions with color data provided for the flowers of plants grown under acidic condition were differences exist. Phenotypic differences may be observed with variations in environmental, climatic, and cultural conditions. The color determination is in accordance with the 2007 R.H.S. Colour Chart of The Royal Horticultural Society, London, England, except where general color terms of ordinary dictionary significance are used.

General description:

*Blooming period.*—Reblooming from June until fall from with removal of spent blooms in Shizuoka, Japan, Niagara on the Lake, Ontario, Canada, and Warsaw, N.C.

*Plant habit.*—Broadly upright, compact, deciduous shrub.

*Height and spread.*—Reaches about 60 cm in height and width on three-year-old plants in a 3-gallon container.

*Hardiness.*—At least to U.S.D.A. Zones 5 to 9.

*Diseases resistance.*—No susceptibility or resistance to diseases has been observed.

*Root description.*—Fine.

Growth and propagation:

*Propagation.*—Softwood stem cuttings.

*Growth rate and vigor.*—Moderate.

Stem description:

*Stem shape.*—Round, solid.

*Stem strength.*—Very strong.

*Stem color.*—New growth; 144B to 144C with lenticels 59A, woody; blend of 164D and N199C.

*Stem size.*—Average of 22 cm (to base of inflorescence), average of 5 mm in width.

*Stem surface.*—Glabrous, slightly glossy, sparsely covered with lenticels; about 5 per square cm, about 1 mm in length and width, becoming bark-like with age.

*Branching.*—Lateral branching is determined by pinching; 2 stems develop per pinched node.

Foliage description:

*Leaf shape.*—Primarily elliptic.

*Leaf arrangement.*—Opposite.

*Leaf division.*—Simple.

*Leaf number.*—Average of 8 (4 pairs) per lateral branch.

*Leaf base.*—Cuneate.

*Leaf apex.*—Cuspidate.

*Leaf margins.*—Serrated, average of 11 per side on a leaf 10 cm in length.

*Leaf venation.*—Penninerved, recessed on upper surface, color 145A on upper surface and lower surface.

*Leaf size.*—Average of 10 cm in length and 5 cm in width.

*Leaf attachment.*—Petiolate.

*Internode length.*—Average of 5.2 cm.

*Leaf surface.*—Glabrous on upper surface, slightly glossy and puberulent on lower surface.

*Leaf color.*—Young foliage upper surface; 137A to 137B, young foliage lower surface; 138B, mature foliage upper surface; 137A to 139A, mature foliage lower surface; 138A.

*Petioles.*—Average of 6 mm in length and 3 mm in width, 145A in color, glabrous surface.

Inflorescence description:

*Inflorescence type.*—Hortensia type (mophead); terminal compound globose corymbs comprised of rotate shaped sterile flowers held above fertile flowers.

*Lastingness of inflorescence.*—Persistent but color is retained for about 4 weeks.

*Inflorescence number.*—One per lateral or sublateral stem if pinched.

*Inflorescence size.*—Average of 9 cm in depth and 13 cm in diameter.

*Flower number.*—Average of 120 sterile flowers and 18 fertile flowers.

*Flower fragrance.*—None.

*Time required to develop an inflorescence.*—Approximately 9 weeks after growth emerges when container grown.

*Flower aspect.*—Upright at stem terminus.

*Flower size.*—Sterile flowers; average of 3 cm in diameter and 4 mm in depth, fertile flowers; average of, fertile flowers; average of 1.2 cm in diameter and 5 mm in depth.

*Flower buds.*—Sterile flowers; average of 4 mm in length and 3 mm in width prior to opening, ovate in shape, 137A in color prior to opening, fertile flowers; average of 2.5 mm in width and diameter, globose in shape, N82C (alkaline soils) or 96C (acidic soils) in color.

*Internode space (between base of inflorescence and last node).*—1 to 1.5 cm in length and about 4 mm in width, color 144B to 144C with lenticels 59A, surface glabrous.

*Peduncles.*—Average of 2.2 cm in length and 1.5 mm in width, color changes from 138C to 73C to 73A (alkaline soils) or 138C to 100B to 100C (acidic soils), glabrous surface.

*Pedicels.*—Sterile flowers; moderate strength, average of 1 cm in length and 1.2 mm in width, typically held at about a 20 to 45° angle from vertical, color changes during development from 138C to 73C to 73A (alkaline soils) or 138C to 100B to 100C (acidic soils), fertile flowers; 5 mm in length and 1 mm in width, 73A in color (alkaline soils) or 100B to 100C (acidic soils) when flower opens, surface glabrous on all flowers.

*Petals.*—Average of 5, present on fertile flowers only, rotate in arrangement, ovate in shape, entire margin, acute apex, truncate base, average of 3 mm in length and 2 mm in width, surface is glabrous and dull on both surfaces, color of upper and lower surface on open flower is 76A to 76B (alkaline soils) or 91A to 91B (acidic soils).

*Sepals.*—Sterile flowers; 4 to 5, orbicular to broadly ovate in shape, average of 1.4 cm in length and 1.6 cm in width, broadly acute to rounded apex, cuneate base, glabrous surface on upper and lower surface, color when grown in alkaline soils: when flower opens upper and lower surface; 144C changing to 145D with blush of 73A, color when flower is fully open upper surface; 73A to 73B, color when flower is fully open lower surface; 73C with veins 73B, eye; 144B changing to 145A changing to 73B, color when grown in acidic soils: when flower opens upper and lower surface; 144C changing to 145D with blush of 100B, color when flower is fully open upper surface; 100B to 100C to 101A, color when flower is fully open lower surface; 100C with veins 100B, eye; 144B changing to 145A changing to 100B, fertile flowers; 5, fused at base into campanulate base (2 m in length and 1.5 mm in width), free segments; rotate in arrangement, glabrous and dull surface (both surfaces), ovate in shape, entire margin, acute apex, average of 2 mm in length and 1 mm in width, color 76B (alkaline soils) or 91B (acidic soils) when fully open.

*Eye* (*fertile flowers*).—144B changing to 145A changing to 73B.

Reproductive organs: (Fertile flowers):

*Stamens*.—Average of 10, anther is oblong in shape, about 1 mm in length and about 197B in color, filament is an average of 4 mm in length and 76C (alkaline) or 91C (acidic) in color, pollen is abundant in quantity and 18D in color.

*Pistils*.—Average of 3, average of 3 mm in length and 0.5 mm in width, stigma is club-shaped and N79A in color, style is an average of 2 mm in length and 70A (alkaline) or 77A (acidic) in color, ovary is inferior and about 145D in color.

*Fruit and seed*.—Has not been observed under the conditions tested to date.

It is claimed:

1. A new and distinct cultivar of *Hydrangea* plant named 'Lapis Lazuli' substantially as herein illustrated and described.

* * * * *